United States Patent
Kimm et al.

(10) Patent No.: US 11,890,415 B2
(45) Date of Patent: Feb. 6, 2024

(54) AIRWAY MANAGEMENT SYSTEMS FOR PULMONARY DISORDER TREATMENT

(71) Applicant: COVIDIEN LP, Mansfield, MA (US)

(72) Inventors: Gardner J. Kimm, Carlsbad, CA (US); Phyllis R. Angelico, San Marcos, CA (US); Jeffrey P. Mansfield, Bloomington, IN (US)

(73) Assignee: Covidien LP, Mansfield, MA (US)

( * ) Notice: Subject to any disclaimer, the term of this patent is extended or adjusted under 35 U.S.C. 154(b) by 398 days.

(21) Appl. No.: 17/198,818

(22) Filed: Mar. 11, 2021

(65) Prior Publication Data

US 2021/0316094 A1    Oct. 14, 2021

Related U.S. Application Data

(60) Provisional application No. 63/009,248, filed on Apr. 13, 2020.

(51) Int. Cl.
  *A61M 16/00* (2006.01)
  *A61M 16/04* (2006.01)

(52) U.S. Cl.
  CPC ...... *A61M 16/024* (2017.08); *A61M 16/0057* (2013.01); *A61M 16/04* (2013.01); *A61M 2205/3375* (2013.01); *A61M 2230/40* (2013.01)

(58) Field of Classification Search
  CPC ............ A61M 16/024; A61M 16/0057; A61M 16/04; A61M 2205/3375; A61M 2230/40
  See application file for complete search history.

(56) References Cited

U.S. PATENT DOCUMENTS

| | | | |
|---|---|---|---|
| 4,326,416 | A | 4/1982 | Fredberg |
| 5,445,144 | A | 8/1995 | Wodicka |
| 6,443,907 | B1 | 9/2002 | Mansy |
| 6,705,319 | B1 | 3/2004 | Wodicka |
| 6,761,693 | B1 | 7/2004 | Rasmussen |
| 7,347,824 | B2 | 3/2008 | Wilkinson |
| 7,708,697 | B2 | 5/2010 | Wilkinson |
| 7,850,618 | B2 | 12/2010 | Wilkinson |
| 8,394,031 | B2 | 3/2013 | Mansy |

(Continued)

OTHER PUBLICATIONS

PCT Notification of Transmittal of the International Search Report and the Written Opinion of the International Searching Authority for International Application No. PCT/US2021/026255 dated Jul. 14, 2021.

(Continued)

*Primary Examiner* — Steven O Douglas

(57) ABSTRACT

A system of treating atelectasis is provided that includes a tracheal tube positioned within an airway of a ventilated patient and an acoustic sensor coupled to the tracheal tube. The system also includes a monitor communicatively coupled to the acoustic sensor. The monitor includes a processor configured to receive a baseline signal from the acoustic sensor. The processor is configured to provide control instructions to adjust a pressure of a gas mixture delivered to the airway through the tracheal tube. The processor is also configured to receive an updated signal from the acoustic sensor after the adjustment and identify a change in airway openness of lungs of the ventilated patient caused by the adjustment of the pressure. Further, identifying the change is based on the baseline signal and the updated signal.

25 Claims, 9 Drawing Sheets

(56) References Cited

U.S. PATENT DOCUMENTS

| | | |
|---|---|---|
| 9,498,590 B2 | 11/2016 | Mansfield |
| 9,707,363 B2 | 7/2017 | Mansfield |
| 10,668,240 B2 | 6/2020 | Mansfield |
| 10,729,621 B2 | 8/2020 | Mansfield |
| 10,780,238 B2 | 9/2020 | Efrati |
| 2011/0265795 A1 | 11/2011 | Tagawa et al. |
| 2019/0038862 A1 | 2/2019 | Mansfield |
| 2019/0224434 A1* | 7/2019 | Silver .................. A61H 31/00 |

OTHER PUBLICATIONS

Admin in Manual Therapist, "Massage for the Patient with a Respiratory Condition", Musculoskeletal Key, Jun. 4, 2016, https://musculoskeletalkey.com/massage-for-the-patient-with-a-respiratory-condition/.

Marini, John J., "Acute Lobar Atelectasis", CHEST Journal, Dec. 5, 2018, pp. 1049-1058, vol. 155, Issue 5, Contemporary Reviews in Critical Care Medicine, https://doi.org/10.1016/j.chest.2018.11.014.

Respiratory Therapy Zone, Postural Drainage Positions and Checst Physiotherapy (CPT) Study Guide, Respiratory Therapy Zone, 2021, https://www.respiratorytherapyzone.com/chest-physiotherapy-positions/.

\* cited by examiner

AIRWAY MANAGEMENT SYSTEMS FOR PULMONARY DISORDER TREATMENT

CROSS-REFERENCE TO RELATED APPLICATION

The present application claims priority to and the benefit of U.S. Provisional Application No. 63/009,248, entitled "AIRWAY MANAGEMENT SYSTEMS FOR PULMONARY DISORDER TREATMENT" and filed Apr. 13, 2020, the specification of which is hereby incorporated by reference in its entirety for all purposes.

BACKGROUND

The present disclosure relates generally to medical devices and, more particularly, to systems, devices, and related methods for monitoring and/or facilitating treatment of pulmonary disorders, such as atelectasis, within ventilated patients.

This section is intended to introduce the reader to various aspects of art that may be related to the present disclosure, as described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air or other gases through a patient's trachea. Such tracheal tubes may include endotracheal (ET) tubes, tracheotomy tubes, or transtracheal tubes. For example, a patient may be intubated when a first end of an endotracheal tube is inserted through the patient's mouth or nose and further inserted into the trachea. Then, a medical provider may couple a ventilator to a second end of the endotracheal tube and utilize the ventilator to mechanically control the type and amount of gases flowing into and out of the patient's airway.

In some situations, mechanically ventilated patients may experience changes in their pulmonary condition over the course of ventilation. In one example, patients may develop atelectasis, which refers to a partial or complete collapse of the lungs that may affect breathing or effectiveness of respiratory gas delivery to the ventilated patients. However, changes in pulmonary condition may be complex to identify in the context of the overlapping clinical conditions of a ventilated patient. Further, the effectiveness of clinical intervention to treat pulmonary disorders is also difficult to assess.

SUMMARY

Certain embodiments commensurate in scope with the originally claimed subject matter are summarized below. These embodiments are not intended to limit the scope of the disclosure. Indeed, the present disclosure may encompass a variety of forms that may be similar to or different from the embodiments set forth below.

In an embodiment, a system includes a tracheal tube positioned within an airway of a ventilated patient and an acoustic sensor coupled to the tracheal tube. The system also includes a monitor communicatively coupled to the acoustic sensor. The monitor includes a processor configured to receive a baseline signal from the acoustic sensor. The processor is configured to provide control instructions to adjust one or more ventilatory parameters to deliver a gas mixture to the airway through the tracheal tube. The processor is also configured to receive an updated signal from the acoustic sensor after the adjustment and identify a change in airway openness of lungs of the ventilated patient caused by the adjustment of the one or more ventilatory parameters. Further, identifying the change is based on the baseline signal and the updated signal.

In an embodiment, a method is provided that includes the steps of receiving, at a ventilator monitor, sensor signals indicative of a sound pressure waveform from an acoustic sensor that is coupled to a tracheal tube positioned within an airway of a ventilated patient. The method includes identifying changes in the sound pressure waveform concurrent with a treatment of atelectasis. Additionally, the method includes providing an indication that the changes are indicative of increasing airway openness, decreasing airway openness, or unchanging airway openness.

In an embodiment, a monitor is configured to control ventilation of a patient. The monitor includes a communication component configured to communicate sensor signals from an acoustic sensor that is coupled to a tracheal tube positioned within a patient airway. The monitor also includes a display and a processor communicatively coupled to the communication component and the display. The processor is configured to receive the sensor signals indicative of a sound pressure waveform from the acoustic sensor. Additionally, the processor is configured to analyze a negative deflection of the sound pressure waveform to determine a state of airway openness of lungs of the patient and instruct the display to provide an indication of the state of airway openness.

In an embodiment, a system is provided that includes a tracheal tube positioned within an airway of a ventilated patient and an acoustic sensor coupled to the tracheal tube. The system also includes a monitor communicatively coupled to the acoustic sensor. The monitor includes a processor configured to receive a signal from the acoustic sensor. The processor is configured to provide control instructions to initiate titration of one or more ventilatory parameters to deliver a gas mixture to the airway through the tracheal tube based on the signal. The processor is also configured to receive updated signals from the acoustic sensor during the titration and identify a setting of the one or more ventilatory parameters associated with sufficient adjustment based on the updated signals from the acoustic sensor.

Features in one aspect or embodiment may be applied as features in any other aspect or embodiment, in any appropriate combination. For example, any one of a system, monitor, ventilator, controller (e.g., processor-based controller), acoustic sensor, or method features may be applied as any one or more other of system, monitor, ventilator, controller, acoustic sensor, or method features.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
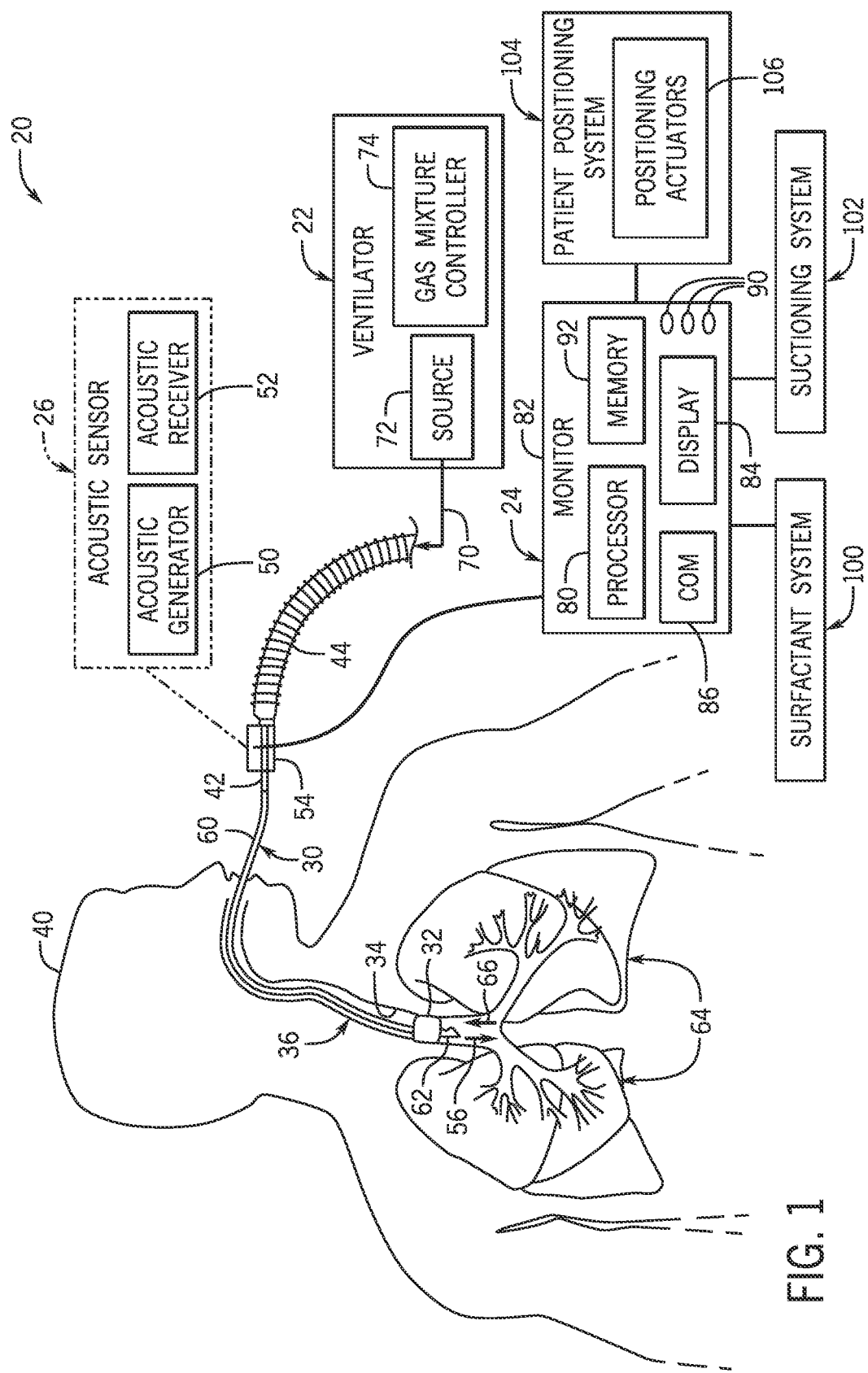
FIG. 1 is a schematic illustration of an implementation of an airway management system including an acoustic sensor and a monitor, in accordance with certain embodiments of the disclosure.

As introduced above, a mechanically ventilated patient may develop atelectasis, which is a pulmonary disorder associated with at least partial closure or collapse of airways within the patient's lungs, thereby reducing a 3-dimensional volume of the lungs. Atelectasis may affect ventilated and unventilated patients, and may be caused by, for example, an outside pressure preventing the lungs from fully expanding, by a lack of natural surfactant within the lungs, infections affecting respiration, atelectrauma, muscle weakness, and/or by an airway blockage, in some cases. During ventilation, a medical provider may couple the ventilator to a tracheal tube that is inserted to and retained at a desired position within the patient's trachea. Then, the ventilator may deliver a gas mixture with patient-specific, cyclic operating ventilatory parameters, such as pressure, volume, flow rate, and/or composition, to the lungs. In some cases, the ventilator controls a ventilator pressure (e.g., inspiratory pressure, pause pressure, and/or positive end expiratory pressure) of the gas mixture to treat atelectasis and facilitate recruitment, or reopening, of a portion of the collapsed airways within the lungs. Moreover, certain premature infants may experience atelectasis that is caused by a lack of surfactant in their underdeveloped lungs. For these infants, the medical provider may instill surfactant to the underdeveloped lungs, reducing surface tension therein and permitting the increased pressure of the ventilator to open or reopen some closed airways. However, changes in response to surfactant treatment occur quickly, and, therefore, the increased pressure may need to be subsequently reduced to account for physiological responses to the surfactant treatment. This timing may vary depending on the patient's individual response, and after-treatment delays in the adjustment of pressure to a lowest pressure to meet ventilatory demand may be associated with undesired lung effects.

For a ventilated patient, treatment of atelectasis via increased ventilator pressure and/or surfactant instillation (or other treatments) may be effective only to a certain degree, after which further increased pressure or surfactant may have limited clinical effect in airways within the lungs that are already open. Because the medical provider may not be aware of whether a treatment is resulting in additional recruitment of airways, the ventilator pressure settings may deviate from an effective treatment and/or ventilation pressure, thus decreasing therapeutic benefits to the ventilated patient. In some instances, the treatment may be effective and the associated increased ventilator pressure may no longer be necessary for effective ventilation. Indeed, the effectiveness of these and/or other treatments for atelectasis may be difficult to discern without repeated and expensive testing, such as chest x-rays, computerized tomography (CT) scans, and so forth. As such, traditional treatments for atelectasis and other similar pulmonary disorders suffer from a lack of instantaneous feedback regarding whether a specific action is successful in recruiting additional airways within the lungs.

With the above in mind, airway management systems are provided herein to facilitate or control treatment of atelectasis or other pulmonary disorders in a ventilated patient based on monitoring and/or identifying characteristic features in an airway acoustic echo of a sound pressure waveform. The airway acoustic echo may be indicative of airway openness or functioning of the airway of the patient. As such, an embodiment of the disclosed airway management system monitors one or more lung parameters of airway openness based on the airway acoustic echo. Further, an embodiment of the disclosed airway management system increases or optimizes airway openness by providing treatments that open or recruit airways that may be affected by atelectasis. To monitor the lung parameters of airway openness, the airway management system includes an acoustic sensor that may be coupled between the tracheal tube and a patient circuit (e.g., hose) of the ventilator. The acoustic sensor may include an acoustic generator that directs sound energy into the tracheal tube and an acoustic receiver that detects reflected sound energy or echoes from the lungs.

Moreover, a monitor of the airway management system is coupled to the acoustic sensor to receive sensor signals from the acoustic receiver and generate sound pressure waveforms including an airway acoustic echo based on the sensor signals, such as based on acoustic reflectometry techniques. The disclosed airway management system determines one or more lung parameters from the airway acoustic echo that provide a patient-specific quantification of a volume of the patient's lung, based on algorithms disclosed herein. Indeed, by analyzing the airway acoustic echoes of the sound pressure waveforms to identify lung parameters before, during, and/or after treatments are provided to the patient, the monitor of the airway management system may assess real-time changes in a degree of atelectasis to provide immediate feedback on the effectiveness of performed treatments.

Further, the airway management system may operate to fine-tune settings for one or more ventilatory parameters, such as pressure, composition, tidal volume and minute volume (in volume operating modalities), peak pressure (in pressure operating modalities), respiratory frequency, positive end expiratory pressure, inspiratory time, inspiratory flow, inspiratory-to-expiratory ratio, time of pause, trigger sensitivity, support pressure, and expiratory trigger sensitivity. In an example, the system can identify a minimum effective setting for the one or more ventilatory parameters to identify a lowest pressure to meet ventilatory demand to address (e.g., identify, treat, correct, and/or prevent reoccurrence of) atelectasis, providing more impactful care to patients than may be possible without the real-time airway openness monitoring discussed herein. In certain embodiments, the airway management system may also facilitate long-term monitoring of a condition of the patient, such as presenting alerts and/or adjusting treatments in response to the lung parameters of airway openness deviating from a stored baseline lung parameters.

FIG. 1 shows an embodiment of an airway management system 20 that includes a ventilator 22, a monitor 24, an acoustic sensor 26, and a tracheal tube 30. The tracheal tube 30 is presently illustrated as an endotracheal tube, which has an inflatable balloon cuff 32 that may be inflated to form a seal against walls 34 of a trachea 36 of a patient 40. However, the tracheal tube 30 may alternatively be uncuffed. Moreover, it should be understood that the airway management system 20 may be used in conjunction with any other suitable types of tracheal tubes or medical devices. As non-limiting examples, the airway management system 20 may be utilized with an endotracheal tube, an endobronchial tube, a tracheostomy tube, an introducer, an endoscope, a bougie, a circuit, an airway accessory, a connector, an adapter, a filter, a humidifier, a nebulizer, nasal cannula, or a supraglottic mask/tube.

As illustrated, the acoustic sensor 26 of the airway management system 20 is coupled to an external or proximal end 42 of the tracheal tube 30. In the illustrated embodiment, the acoustic sensor 26 may operate as or be an adapter that facilitates coupling of the tracheal tube 30 to a patient circuit 44 or hose of the ventilator 22. However, other arrangements are also contemplated, such as an acoustic sensor 26 that is disposed on the tracheal tube 30 or on other components of the breathing circuit. The acoustic sensor 26 includes at least one acoustic generator 50 and at least one acoustic receiver 52 disposed within an adapter housing 54. The acoustic generator 50 is oriented to direct sound energy 56 (e.g., sound, acoustic energy) into a body 60 of the tracheal tube 30, which guides the sound energy 56 out of an internal or distal end 62 of the tracheal tube 30 and toward airways of lungs 64 of the patient 40. Further, the acoustic receiver 52 detects any reflected sound energy 66, or echoes of the sound energy 56, back from the airways of the lungs 64. Accordingly, the acoustic sensor 26 facilitates acoustic reflectometry techniques that may analyze sound pressure waveforms for airway acoustic echoes indicative of airway openness. That is, the acoustic generator 50 and the acoustic receiver 52 cooperate to provide sensor signals indicative of a sound pressure waveform having an airway acoustic echo, which the monitor 24 may analyze to determine lung parameters indicative of airway openness or the volume within the lungs 64, as discussed in more detail below.

The acoustic generator 50 of some embodiments is a speaker or a miniature speaker. However, the acoustic generator 50 may additionally or alternatively include any suitable loudspeakers, buzzers, horns, sounders, and so forth that rely on moving coil, electrostatic, isodynamic, or piezoelectric techniques. Additionally, the acoustic receiver 52 may be a microphone, microphone array, or other sound pressure sensors, in some embodiments. When implemented as a microphone array, the acoustic receiver 52 and/or the monitor 24 discussed below may be designed to sense the direction from which sound energy is received and therefore isolate or filter out any interfering sound energy that is not a reflection of the emitted sound energy 56 provided by the acoustic generator 50. Moreover, it should be understood that any other suitably paired components that respectively generate suitable sound energy and receive echoes or reflection of the sound energy may be used in the acoustic sensor 26. Further, in some embodiments, the acoustic sensor 26 is an AirWave™ adaptor by SonarMed, Inc. of Carmel, IN.

The airway management system 20 also includes devices that facilitate positive pressure ventilation of the patient 40, such as the ventilator 22, which may include any ventilator that provides mechanical ventilation to the patient 40. For example, the ventilator 22 may provide a gas mixture 70 (e.g., from a source 72 of the gas mixture 70) through the acoustic sensor 26, through the tracheal tube 30, and to lungs 64 of the patient 40, thereby mechanically actuating rest, inspiration, and expiration phases of breathing cycles of the patient 40. In some embodiments, the ventilator 22 includes a gas mixture controller 74 that provides control instructions to cause the ventilator 22 to continuously or intermittently adjust a pressure and/or a composition of the gas mixture 70 provided from the source 72 and to the patient 40. For example, the gas mixture controller 74 may cause the ventilator 22 to direct air, oxygen, or another suitable gas mixture from the source 72 to the lungs 64 of the patient 40.

In the illustrated embodiment, the monitor 24 is communicatively coupled to the acoustic sensor 26 and the ventilator 22 to implement embodiments of the present disclosure. Indeed, the monitor 24 may analyze the sensor signals from the acoustic sensor 26 via acoustic reflectometry techniques to monitor the lung parameters indicative of airway openness of the patient 40. Thus, as discussed below, the monitor 24 may provide immediate feedback to identify atelectasis as well as response to any atelectasis treatments (e.g., ventilatory parameter adjustment, bronchodilation, surfactant, patient repositioning) performed on the patient 40. In certain embodiments, the monitor 24 may also provide control instructions to the ventilator 22 (e.g., automatically) to instruct the ventilator 22 to perform certain atelectasis treatments in an effective or optimized manner. However, in other embodiments, the monitor 24 does not electronically communicate with the ventilator 22. In any case, the monitor 24 may be designed to provide indications of lung parameters of airway openness, such as an audio, visual, or other indication, and/or may be configured to communicate the information to another device. In an embodiment, based at least in part upon the received signals from the acoustic sensor 26, a processor 80 of the monitor 24 may determine lung parameters using various algorithms disclosed herein. In general, such algorithms will be stored in non-transitory computer media (e.g., memory) and executed by the processing circuitry as described below. Further, in embodiments of the airway management system 20 in which the acoustic receiver 52 includes a microphone array, the monitor 24 may filter out signals associated with the ventilator 22 or other sounds or vibrations emitted from outside the body of the patient 40. In an embodiment, the monitor 24 may analyze the lung parameter during rest phases of the patient's breathing cycles to further reduce background noise, thereby providing updated indications of airway openness for every breath of the patient 40 (e.g., every second or few seconds).

It should be understood that the monitor 24 may be a stand-alone device or may, in embodiments, be integrated into a single device with another medical device, such as the ventilator 22. Coupled to or disposed within a monitor housing 82, the monitor 24 may include a display 84, at least one communication component 86 (e.g., input/output ports, communication circuitry), user-selectable buttons 90, a memory 92, and processing circuitry, such as the processor 80, that are all communicatively coupled to one another to facilitate the present techniques. The medical provider may provide inputs to the monitor 24 via the user-selectable buttons 90 and/or via a sensor (e.g., a capacitive touch screen sensor on the display 84, or other mechanical or capacitive buttons or keys on the monitor housing 82). The processor 80 may include one or more microprocessors, one or more application specific integrated circuits (ASICs), one or more general purpose processors, one or more controllers, one or more programmable circuits, or any combination thereof. For example, the processor 80 of the monitor 24 may also include or refer to control circuitry for the display 84. The memory 92 may include volatile memory, such as random access memory (RAM), and/or non-volatile memory, such as read-only memory (ROM). Moreover, the processor 80 may execute instructions that are stored in the memory 92. The monitor 24 may be configured to communicate with the acoustic sensor 26, the ventilator 22, and/or any other components of the airway management system 20 via any suitable communication protocols, such as via wired connections, WI-FI®, or BLUETOOTH®.

By interoperating the various components therein, the airway management system 20 may monitor, facilitate, or automatically provide one or multiple atelectasis treatments to the patient 40 in an efficient manner that increases or optimizes lung parameters indicative of airway openness of the lungs 64. The display 84 provides qualifications and/or quantifications of the airway openness that offer immediate feedback on any treatments, which may be automatically instigated by the monitor 24 and/or manually performed by a medical provider. Indeed, it should be understood that any suitable treatment schedule, including a single treatment or a combination of multiple treatments, may be monitored and/or actuated by the monitor 24. For example, the monitor 24 may directly actuate treatments by providing control signals to other components or treatment subsystems of the airway management system 20 and/or may provide indications via the display 84 to the medical provider to recommend that treatments be initiated, adjusted, or stopped. In some embodiments, the monitor 24 may also receive user input indicative of performed treatments, which may be stored within a patient-specific log in the memory 92 to permit tracking of the treatment history of the patient 40.

As particular examples of operation of certain treatment subsystems, the monitor 24 (e.g., processor 80) of the airway management system 20 may provide control instructions to the gas mixture controller 74 of the ventilator 22 to adjust settings of one or more ventilatory parameters, such as the pressure and/or the composition of the gas mixture 70 delivered to the patient 40, tidal volume and minute volume (in volume operating modalities), peak pressure (in pressure operating modalities), respiratory frequency, positive end expiratory pressure, inspiratory time, inspiratory flow, inspiratory-to-expiratory ratio, time of pause, trigger sensitivity, support pressure, and expiratory trigger sensitivity. For example, by increasing the pressure of the ventilator 22, certain closed airways within the lungs 64 may be recruited. Additionally, a portion of the closed airways may be recruited by adjusting the composition of the gas mixture 70 to selectively include a bronchodilator or other inhaled medication (e.g., a mucolytic that helps break down secretions that if once removed, may help resolve atelectasis caused by obstructions) for a threshold period (e.g., include a bronchodilator or other inhaled medication for 10 minutes every four hours). In some embodiments, the airway management system 20 may also include a surfactant system 100 having a surfactant source and a surfactant actuator (e.g., control valve, piston) that are operatively coupled to the ventilator 22, where the monitor 24 may instruct the surfactant actuator to instill a threshold amount of a natural or synthetic surfactant to the lungs 64 (e.g., via the tracheal tube 30). Moreover, a suctioning system 102 (e.g., including an actuatable vacuum coupled to storage vessel) may be provided within the airway management system 20 to receive control instructions from the monitor 24 to automatically suction the airway of the patient 40. In other embodiments, the surfactant system 100 and/or the suctioning system 102 may be manually controlled by the medical provider to provide atelectasis treatments. In an embodiment, the surfactant system 100 and/or the suctioning system 102 may be separate from the airway management system 20. The suctioning system 102 may be closed via integration with the patient breathing circuit or may be open and introduced directly through the tracheal tube 30. Surfactant solution can be instilled in one of several ways through the tracheal tube 30, such as through a port or directly through the acoustic sensor 26. In an embodiment, subsequent to surfactant instillation, the ventilator circuit can be re-attached to the airway immediately to monitor in real-time increased openness based on signals from the acoustic sensor 26.

As another possible treatment subsystem, the airway management system 20 may include a patient positioning system 104 having one or more positioning actuators 106 that are configured to reposition the patient 40 relative to a bed (e.g., electronically-controlled medical bed) or other surface on which the patient 40 is placed. For example, in response to rotating the patient 40 relative to the bed, the patient's weight may be redistributed to alleviate external pressure applied to particular portions of the lungs 64, making certain airways more susceptible to recruitment. As non-limiting examples, the monitor 24 may automatically instruct the positioning actuators 106 to position the patient between a supine position, a prone position, a left lateral recumbent position, a right lateral recumbent position, and so forth. Accordingly, by providing real time assessment of lung parameters for airway openness (e.g., corresponding to an extent of atelectasis) during any suitable atelectasis treatments, the monitor 24 may facilitate improved treatments that recruit more airways within the lungs 64 than may have been possible without the airway management system 20.

Figure 2:
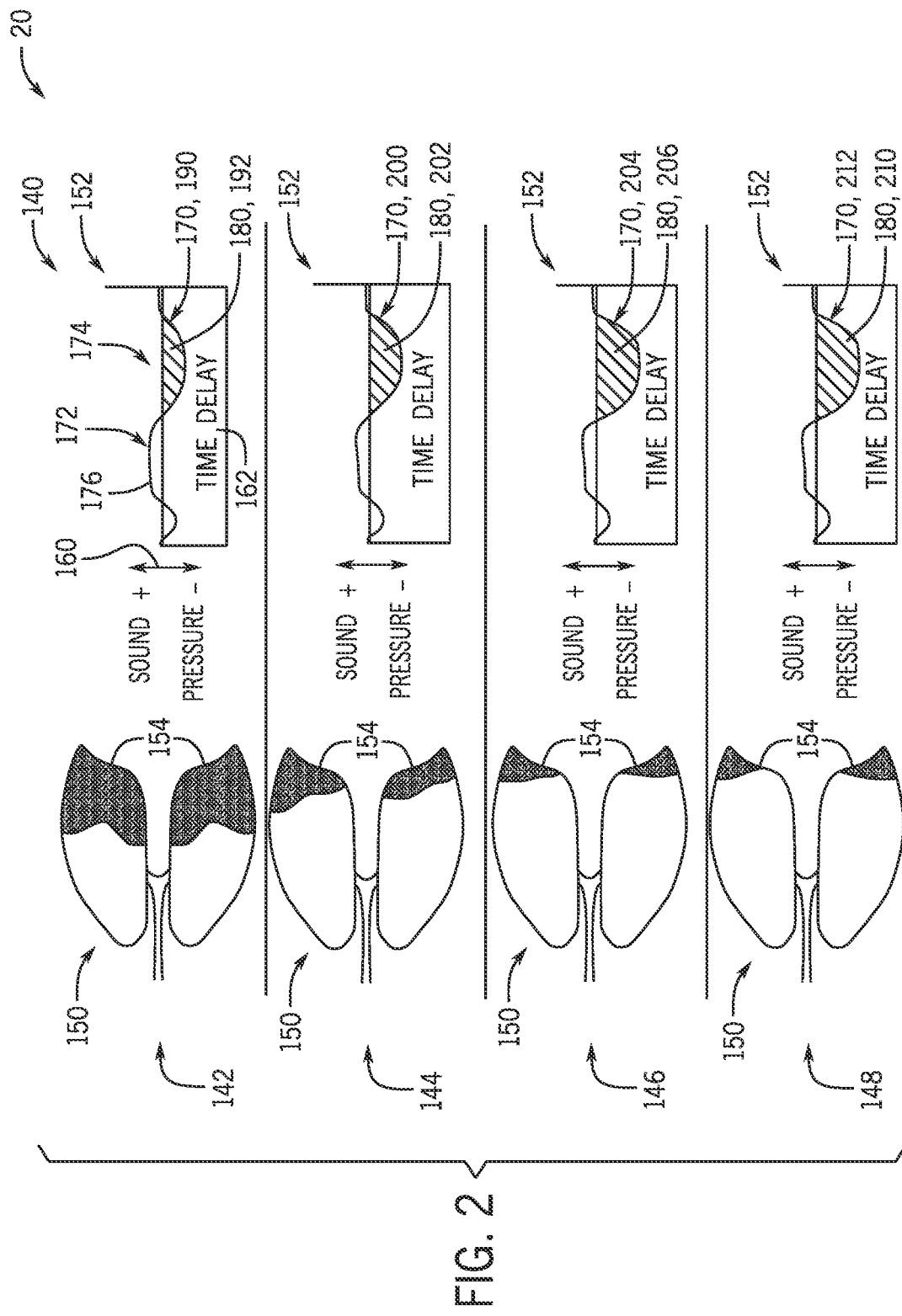
FIG. 2 is a schematic illustration of sound pressure waveforms based on feedback from the acoustic sensor of FIG. 1 over a course of a treatment for atelectasis, in accordance with certain embodiments of the disclosure.

FIG. 2 is a schematic diagram illustrating a sequence of measured sound pressure waveforms over an atelectasis treatment process 140, as monitored and/or facilitated by the airway management system 20. In each of a first time period 142, a second time period 144, a third time period 146, and a fourth time period 148, a respective lung representation 150 depicting different states of airway openness as discussed herein is associated with a sound pressure waveform 152 detected and analyzed by the monitor 24 discussed above. Respective shaded portions 154 of the lung representations 150 may correspond to closed airways indicative of an extent of atelectasis in the respective time period. The sound pressure waveforms 152 may be captured by the acoustic receiver 52 of the acoustic sensor 26 based on the reflected sound energy 66 from the patient's airway, via acoustic reflectometry. As such, the sound pressure waveforms 152 are presently illustrated as an echo diagram of sound pressure amplitude 160 by time delay 162, where structures providing acoustic echoes that are further along an x-axis, representing the time delay 162, are positioned within the airway further from the acoustic sensor 26. However, it should be understood that any suitable graphical representation may be generated based on the sensor signals from the acoustic sensor 26, in accordance with the present techniques and based on the particular extent of atelectasis. Further, the lung representations 150 are provided by way of example to illustrate stages of airway openness that are associated with different example characteristic sound pressure waveforms 152 in a patient and may or may not be generated or provided by the system 20. However, in an embodiment, the airway management system 20 may provide a graphical indication of airway openness, such as the lung representation 150.

In more detail, the reflected sound energy 66 or echoes may be sensed by the acoustic receiver 52 of the acoustic sensor 26 in response to the sound energy 56 (as illustrated in FIG. 1) contacting a change in cross-sectional area within the patient's airway. For example, in response to the sound energy 56 encountering a decrease in cross-sectional area (e.g., associated with a reduction in area from the acoustic sensor 26 to the tracheal tube 30), the reflected sound energy 66 may form a positive deflection at a corresponding time delay within the sound pressure waveforms 152. Alternatively, in response to the sound energy encountering an increase in cross-sectional area (e.g., associated with an increase in area from the tracheal tube 30 to the lungs 64), the reflected sound energy 66 may form a negative deflection at a corresponding time delay within the sound pressure waveforms 152.

Because the lungs 64 and associated airways are located further from the acoustic sensor 26 than the tracheal tube 30 and the trachea 36, the sound pressure waveforms 152 may include a portion representative of an airway acoustic echo 170 that reflects a greater time delay than a portion representative of a tube or trachea acoustic echo 172 of the sound pressure waveforms 152. Moreover, because the airway passages within the lungs may collectively form a greater cross-sectional area than the trachea 36, the airway acoustic echo 170 may be indicative of a comparatively larger negative deflection of the sound pressure waveform 152. As such, the airway acoustic echo 170 may be identified based on its time position subsequent to the trachea acoustic echo 172 of the sound pressure waveforms 152 and/or, in certain embodiments, other components of the signal such as an expected amplitude shift from positive to negative between the trachea acoustic echo 172 and the airway acoustic echo 170.

The monitor 24 may analyze the airway acoustic echo 170 of each sound pressure waveform 152 to determine one or more lung parameters indicative of a state of airway openness or functioning of airways within the lungs 64. Indeed, as recognized herein, the area above the curve (e.g., integral, negative area) of the negative deflection that is identified as the airway acoustic echo 170 may directly correlate to the volume of open airways within the lung (i.e., the sum of cross-sectional areas of the airways). As such, by integrating the negative deflection, or calculating the area above the curve or echo signal 176 of the airway acoustic echo 170 (e.g., between the time delay or x-axis and the echo signal 176), the monitor 24 may determine a lung parameter 180 that quantifies the airway openness of the patient 40. In the illustrated embodiment, the lung parameter 180 corresponding to the integral of the associated airway acoustic echo 170 is represented by a shaded portion within the respective sound pressure waveform 152. However, it should be understood that additional lung parameters, such as those associated with the specific amplitudes, slopes, and/or time delays of the airway acoustic echo 170, may also be analyzed by the monitor 24 disclosed herein.

With the above understanding in mind, during the first time period 142, a baseline airway acoustic echo 190 is integrated to provide a baseline lung parameter 192. The baseline lung parameter 192 may represent the total cross-sectional area (e.g., sum of cross-sectional areas representing volume) of any initially open airways, such as before any treatments are performed and/or while the ventilator 22 is operating at initial settings. Because the patient 40 may be experiencing atelectasis in at least a portion of the lungs, as illustrated by the shaded portions 154 of the lung representation 150, the baseline lung parameter 192 may be a comparatively small value, having units of squared sound pressure (e.g., $Pa^2$). Then, during or after a first treatment (e.g., increased positive ventilator pressure), a second airway acoustic echo 200 may be analyzed during the second time period 144 to provide a second lung parameter 202. In the present example, the first treatment is at least partially effective in reducing atelectasis, as illustrated by the relatively smaller shaded portions 154 of the lung representation 150 in the second time period 144. As such, the second airway acoustic echo 200 is increased in negative amplitude, such that the second lung parameter 202 is greater than the baseline lung parameter 192 and that the lungs 64 have a greater open total cross-sectional area resulting from airway recruitment.

Further, during or after a second treatment, a third airway acoustic echo 204 may be analyzed during the third time period 146 to provide a third lung parameter 206. Similar to the first treatment above, the illustrated example shows that the second treatment was also successful in recruiting additional airways, such that the shaded portion 154 of the lung representation 150 is reduced in the third time period 146 relative to the second time period 144. Within the subsequent fourth time period 148 that is during or after a third treatment, analysis of a fourth lung parameter 210 determined from a fourth airway acoustic echo 212 may reveal that the third treatment did not recruit additional airways within the lungs 64. In other words, the fourth lung parameter 210 may be substantially equal to the third lung parameter 206 (e.g., not different by more than a threshold amount, within 5%). In an embodiment, if the non-recruiting treatment was an increase in ventilator pressure, the monitor 24 may provide control signals to cause the ventilator 22 to decrease or decrement the pressure back to a previous ventilator pressure that was provided before the increased ventilator pressure. Based on these acoustic reflectometry techniques, the monitor 24 analyzing the sound pressure waveforms 152 may immediately provide feedback during or after any suitable atelectasis treatments to facilitate efficient reduction of atelectasis and increase in lung volume.

Figure 3:
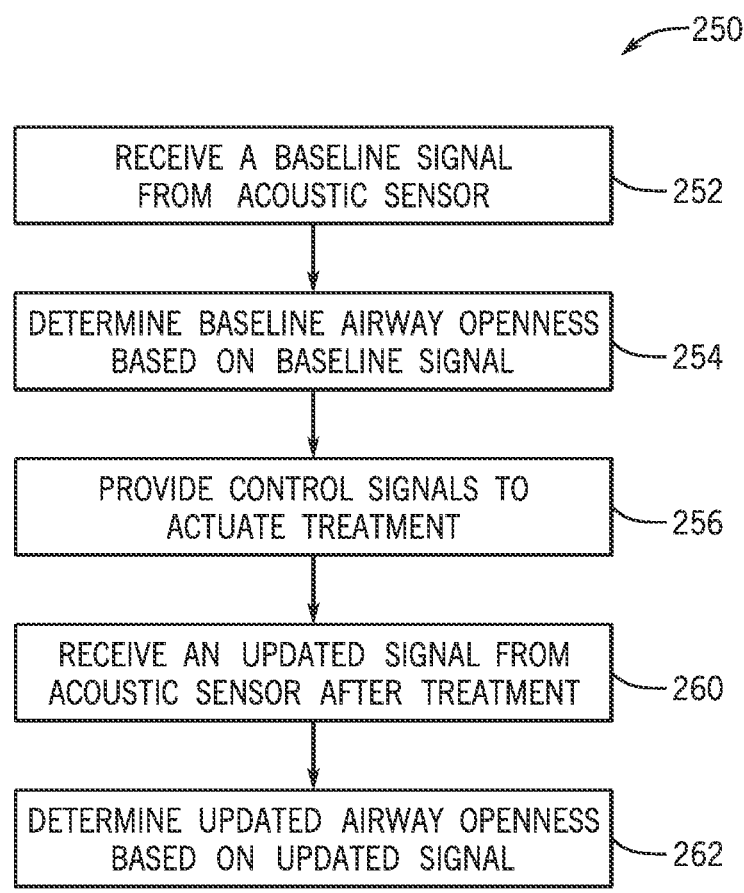
FIG. 3 is a flow diagram of a method of operating the airway management system of FIG. 1 to provide an atelectasis treatment for a ventilated patient, in accordance with certain embodiments of the present disclosure.

With the above understanding of the components and general operation of the airway management system 20 in mind, further discussion is provided herein regarding certain processes of operating example embodiments of the airway management system 20, along with certain illustrative user interfaces. For example, FIG. 3 is a flow diagram of a method 250 of treating atelectasis within the patient 40, in accordance with some embodiments. The method is generally indicated by reference number 250 and includes various steps or actions represented by blocks. It should be noted that the method 250 may be performed as an automated procedure by a system, such as the airway management system 20. Further, certain steps or portions of the method 250 may be performed by separate devices. For example, in some embodiments, a first portion of the method 250 may be performed by the monitor 24, while a second portion of the method 250 may be performed by the ventilator 22, the gas mixture controller 74, and/or any other suitable treatment subsystems (e.g., the surfactant system 100, the suctioning system 102, the patient positioning system 104). In some embodiments, portions of the method 250 may be performed continuously or intermittently for long-term patient monitoring and/or treatment or at any appropriate interval depending on the particular situation of the ventilated patient. Although generally discussed below with reference to the monitor 24 performing the steps of the method 250, it should be understood that the various components of the monitor 24, including the processor 80 and memory 92 therein, may interoperate to facilitate the present techniques.

As illustrated, the present embodiment of the method 250 begins with the monitor 24 receiving, at step 252, an initial or baseline signal (e.g., sensor signal) from the acoustic sensor 26. As discussed above, the acoustic sensor 26 may be coupled to the tracheal tube 30 that is positioned within the airway of the patient, who may be mechanically ventilated via the ventilator 22. For example, the monitor 24 may receive the baseline signal in response to the acoustic sensor 26 being powered on, being communicatively coupled to the monitor 24 (e.g., via wired or wireless pairing), being interrogated by the monitor 24 (e.g., automatically, regularly, based on user input requesting transmission of the baseline signal), and/or in response to any other suitable conditions being met. In some embodiments, the monitor 24 may receive the baseline signal and any subsequent sensor signals from the acoustic sensor 26 during respective rest phases of the breathing cycles actuated by the ventilator 22. Indeed, the acoustic sensor 26 may automatically provide sensor signals to the monitor 24 on a regularly scheduled basis, which may align with the respective rest phases.

With the baseline signal received, the monitor 24 may determine, at step 254, a baseline airway openness of the patient 40 from the baseline signal. For example, the monitor 24 may determine or generate a baseline sound pressure waveform from the baseline signal, which includes the baseline airway acoustic echo 190 discussed above. The monitor 24 of certain embodiments may analyze or integrate the baseline airway acoustic echo 190 to determine the baseline lung parameter 192, which may be indicative of the baseline airway openness of the patient 40. Indeed, by taking the area above the curve (e.g., between the negative deflection and time delay axis) of the baseline acoustic echo 190, the monitor 24 may quantify the baseline lung parameter 192 as a baseline or reference point for the state of airway openness. Further, certain embodiments may analyze multiple baseline signals over a threshold time period or threshold number of signals to determine an average lung parameter as the baseline lung parameter 192, thereby improving the precision of the baseline airway openness determination performed before treatment.

The monitor 24 may issue or provide control signals to identify atelectasis, provide a notification related to the atelectasis, and/or automatically adjust one or more ventilatory parameters or initiate other actions to treat atelectasis. As a non-limiting example, the processor 80 of the monitor 24 may, at step 256, provide control signals to the ventilator 22 to cause the ventilator 22 to adjust one or more ventilatory parameters, such as gas mixture composition, pressure, tidal volume, minute volume, peak pressure, respiratory frequency, positive end expiratory pressure, inspiratory time, inspiratory flow, inspiratory-to-expiratory ratio, time of pause, trigger sensitivity, support pressure, expiratory trigger sensitivity, or a combination thereof. The processor 80 may additionally or alternatively provide control signals to instruct the surfactant system 100 to instill surfactant to the patient's airway, control signals to instruct the suctioning system 102 to clear the patient's airway, or control signals to instruct the patient positioning system 104 to adjust a bodily position of the patient 40.

Additionally or alternatively, in other embodiments, the processor 80 may provide the control signals to the display 84 of the monitor 24, which presents indications that instruct the medical provider to manually provide any suitable treatments, such as selection of an available recruitment mode setting on the ventilator, manual suctioning or surfactant instillation, repositioning, etc. For example, in situations in which the monitor 24 does not communicate with the ventilator 22, the monitor 24 may present the indications recommending that the medical provider manually adjust settings of the ventilator 22.

In an embodiment, the airway management system 20 may receive or determine a position of the tracheal tube 30 before initiating the atelectasis treatment (e.g., adjustment of ventilatory parameters). In some cases, the identified airway openness decrease based on the sensor signal may be associated with tracheal tube misplacement, such as in the right mainstem bronchus, rather than atelectasis. Increase of ventilatory pressure in the case of tracheal tube misplacement is undesired. Accordingly, the disclosed techniques may include determination of tracheal tube position and/or identification changes in tracheal tube position and rules that initiate treatment or notifications contingent upon identification of a decrease in airway openness concurrent with no associated tracheal tube misplacement or movement (beyond a preset tolerance) relative to a baseline position. In an embodiment, the tracheal tube position may be determined based on the signal from the acoustic sensor 26.

At step 260, the monitor 24 may receive an updated signal from the acoustic sensor 26. In an embodiment, the monitor 24 may continuously receive sensor signals from the acoustic sensor 26 during the ventilation of the patient 40, such that the monitor 24 automatically receives the updated signal during and subsequent to the treatment actuated at step 256. Alternatively, the monitor 24 may instruct the acoustic sensor 26 to provide the updated signal in response to the monitor 24 determining that a treatment has been performed (e.g., a threshold time period after the monitor 24 sends control signals, in response to user input). In any case, the monitor 24 may determine, at step 262, an updated airway openness of the patient 40 from the updated signal, in a manner similar to the processing steps discussed above with reference to step 254. In brief, by analyzing the airway acoustic echo 170 of an updated sound pressure waveform determined from the updated signal, the monitor 24 may determine an updated lung parameter that quantifies the updated airway openness to provide real-time atelectasis treatment monitoring.

Figure 4:
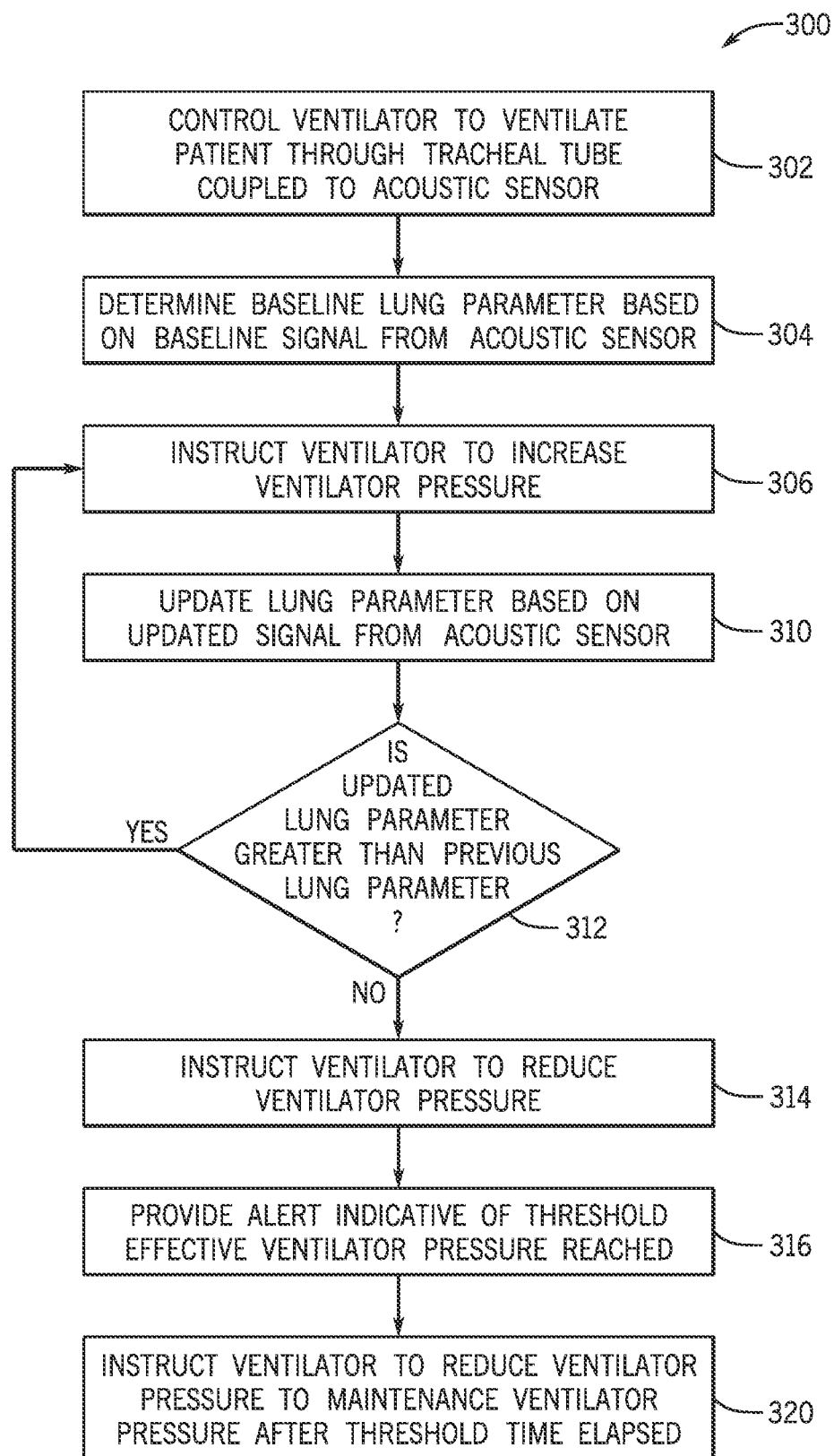
FIG. 4 is a flow diagram of a method of operating the airway management system of FIG. 1 for use in conjunction with a closed control loop ventilator, in accordance with certain embodiments of the present disclosure.

As a more particular example, FIG. 4 is a flow diagram of a method 300 for determining (e.g., automatically determining) an effective ventilator pressure for treating atelectasis with the airway management system 20. The method is generally indicated by reference number 300 and includes various steps or actions represented by blocks, which may be performed by the processor 80 of the monitor 24, in an embodiment. In the illustrated example, the method 300 is started by the processor 80 controlling, at step 302, the ventilator 22 to ventilate the patient 40. For example, the processor 80 may actuate the ventilator 22 to provide the gas mixture 70 to the patient 40 at initial ventilator settings, which are calibrated by the medical provider. The acoustic sensor 26, which is coupled to the tracheal tube 30 positioned within the patient's airway, may provide sensor signals to the monitor 24. Thus, for the ventilated patient 40, the monitor 24 may determine, at step 304, the baseline lung parameter based on one or more baseline sensor signals provided by the acoustic sensor 26, as discussed above.

Further, at step 306, the processor 80 may provide control signals to instruct the ventilator 22 to increase (e.g., adjust) the ventilator pressure as an atelectasis treatment. While the disclosed embodiment is discussed in the context of ventilatory pressure changes, additionally or alternatively, the processor 80 may provide control signals to adjust one or more ventilatory parameters such as gas mixture composition, pressure, tidal volume, minute volume, peak pressure, respiratory frequency, positive end expiratory pressure, inspiratory time, inspiratory flow, inspiratory-to-expiratory ratio, time of pause, trigger sensitivity, support pressure, or expiratory trigger sensitivity. In one embodiment, the processor 80 may instruct the ventilator 22 to initiate a preprogrammed operating mode, such as a recruitment maneuver, that includes the appropriate parameter adjustment instructions. The processor 80 may instruct the ventilator 22 to increase the ventilator pressure, or other ventilatory parameter by a threshold increment amount, by a threshold increment percentage (e.g., 5 percent), and so forth.

After the ventilator pressure is increased, the processor 80 may update, at step 310, the lung parameter based on updated signals received from the acoustic sensor 26. For example, the processor 80 may analyze an updated airway acoustic echo of an updated sound pressure waveform to determine a current value of the lung parameter, which directly represents or quantifies the open total cross-sectional area (e.g., volume, lung volume) of the patient's airway. At step 312, the processor 80 may determine whether the updated lung parameter is greater than the previous lung parameter. However, other embodiments may analyze whether the updated lung parameter is greater than the previous lung parameter by a threshold amount or a threshold percentage difference (e.g., 5 percent difference). In one embodiment, the adjustment may be programmed based on the observed response from the acoustic sensor 26. If limited or no recruitment is observed after one or more cycles after initiating adjustment, a larger adjustment step may then occur. If, after a few cycles and a larger adjustment, no response (i.e., change in airway openness) is observed, the method 300 may provide a notification to try an alternate treatment.

However, if the adjustment appears to change the airway openness, in response to determining that the updated lung parameter is greater than previous lung parameter (e.g., by a threshold amount, predetermined amount, or percentage difference), the processor 80 may identify that the increased ventilator pressure is effective in recruiting additional airways, and, thus, return to step 306 to provide control signals that instruct the ventilator 22 to again increase or increment the ventilator pressure. As such, in a closed loop control manner, the monitor 24 of the airway management system 20 iteratively continues to cause the ventilator pressure to increase, provided that additional airways within the lungs 64 are recruited by the increased pressure.

After a certain number of cycles of ventilatory parameter (e.g., pressure increase) adjustment, a plateau of effectiveness may be reached that is indicative of sufficient adjustment. In an embodiment, the processor 80 may be programmed to wait a predetermined amount of time or to cycle through at least a predetermined number of increases or parameter adjustments before determining that the recruitment has occurred. In response to determining that the updated lung parameter is not greater than the previous lung parameter and that is indicative of an effectiveness plateau, the processor 80 may provide control signals to instruct the ventilator 22 to maintain or reduce the ventilator pressure, at step 314 after recruitment has occurred.

For example, the processor 80 may instruct the ventilator 22 to return to a previous pressure setting that was applied prior to the increased pressure of the most recent iteration of step 306, which may correlate to a threshold effective pressure of the ventilator 22. Simultaneously or subsequently, the processor 80 may provide, at step 316, an alert indicating that the threshold effective ventilator pressure (e.g., minimum effective ventilator pressure) for treating atelectasis is reached. In other words, because the increased ventilator pressure did not result in further recruitment, the monitor 24 identifies that further increased pressure may not be beneficial for the particular patient 40 (e.g., without a supplemental atelectasis treatment, such as surfactant instillation, patient repositioning, bronchodilator application, or suctioning). Further, at step 320, the processor 80 may provide control instructions to instruct the ventilator 22 to further reduce the ventilator pressure to a lower maintenance pressure, such as after a threshold treatment time period has elapsed. Indeed, by providing the threshold effective ventilator pressure for the threshold treatment time, then reducing the pressure to a lower maintenance ventilator pressure, the airway management system 20 may deliver an effective atelectasis treatment for a targeted length of time that reduces potential over-pressurizing effects to the airways that are open or have been reopened.

These instructions may, in an embodiment, be contingent on a verification step that assesses a persistence of the recruitment effect. For example, any stepwise reduction or return to baseline ventilatory parameters before the adjustment may only occur after a predetermined time period of stability of airway openness. If there is instability in the airway openness (lung parameter), then the cycles of parameter adjustment in the method 300 may be repeated. In one example, an increase in tidal volume (in a pressure control mode of ventilation) should be observed with recruitment. When the pressure parameter is stepped back, the tidal volume should remain increased to some degree from before pressure was increased. If not, the lowered pressure could be associated with derecruitment. Accordingly, the tidal volume, in a pressure control mode of ventilation, may be used as an indicator of whether the adjustment is sufficient and whether the recruitment is persistent. If the tidal volume remains increased even after stepping back on pressure, then the recruitment is persistent. If the tidal volume is not increased, the method may reinitiate cycles of parameter adjustment. If a volume control mode, the pressure to deliver the volume should decrease if recruitment is achieved, and this decrease may be used as an indicator of persistence of the recruitment effect and sufficient adjustment.

Figure 5:
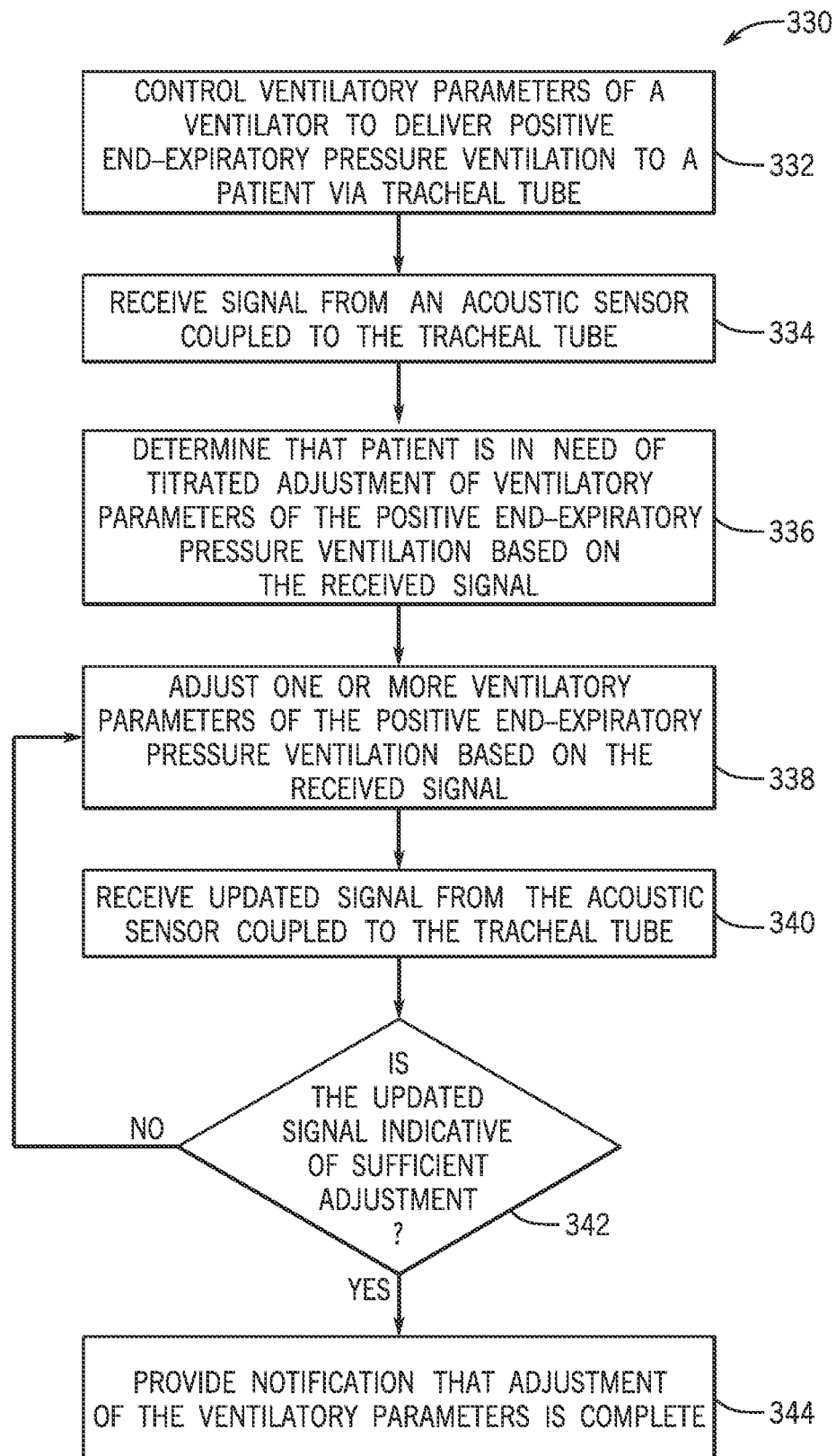
FIG. 5 is a flow diagram of a method of operating the airway management system of FIG. 1 for use in conjunction with positive end-expiratory pressure ventilation, in accordance with certain embodiments of the present disclosure.

FIG. 5 is a flow diagram of a method 330 for use in conjunction with the system 100 coupled to a ventilator controlled to deliver positive end-expiratory pressure (PEEP) to a ventilated patient via a tracheal tube (step 332). In PEEP ventilation, the airway pressure is maintained above atmospheric pressure at the end of exhalation to oppose passive emptying of the lungs. For example, PEEP ventilation may include applied end-expiratory pressure of less than 5 cm $H_2O$ or, at higher levels, greater than 5 cm $H_2O$. A signal is received from an acoustic sensor (acoustic sensor 26, see FIG. 1) coupled to the tracheal tube (step 334). Based on the signal, the system 100 identifies that the patient is in need of adjustment of one or more ventilation parameters as provided herein (step 336). The method 330 initiates a titrated adjustment of one or more of the PEEP ventilation parameters (step 338). The titrated adjustment may be a stepwise or incremental adjustment performed iteratively. As mentioned, the titrated adjustment may be based on a single ventilation parameter, in an embodiment. Upon receiving updated sensor signals (step 340) concurrent with the titration, the system 100 determines if the updated sensor signal indicates that sufficient adjustment has occurred to achieve desired recruitment and changes in airway openness (step 342). If the adjustment is insufficient, the method 330 iterates back to continue the titration. However, if the adjustment is determined to be sufficient, the method provides a notification of completion of the adjustment (step 344). As such, a lowest PEEP ventilation setting (e.g., ventilation parameter) may be reached that achieves target or desired opening of previously closed lung passages.

In one example, the adjustment of the parameter includes a stepwise titration of the PEEP pressure to a relatively higher level (e.g., 20-25 cm $H_2O$) and maintained at the adjusted pressure for predetermined amount of time. The adjusted pressure may be determined based on the relationship between changes in the lung parameter determined from the sensor of the acoustic sensor 26, whereby continued increases in airway openness indicate that the titration may be continued within preset limits. Following the increase, the PEEP pressure may be decremented in conjunction with confirmation of persistent recruitment effect as provided herein. The adjustment of the PEEP pressure may be in conjunction with adjustment of one or more other ventilatory parameters.

Figure 6:
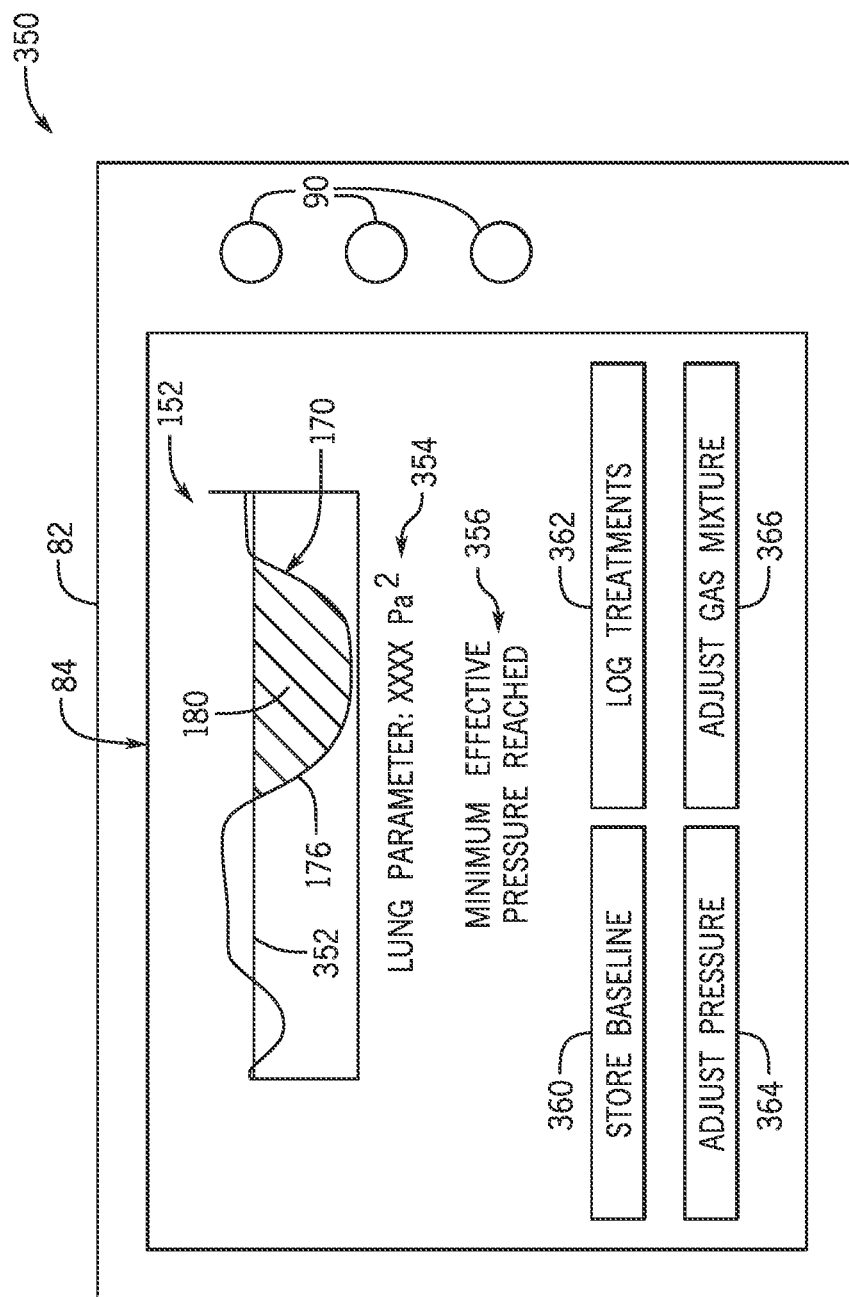
FIG. 6 is a schematic illustration of a user interface for the monitor of the airway management system of FIG. 1 that includes airway openness indicators, in accordance with certain embodiments of the present disclosure.

FIG. 6 is a schematic illustration of a user interface 350 for the display 84 of the monitor 24 that includes a generated representation of the sound pressure waveform 152, the airway acoustic echo 170, and the lung parameter 180 determined as the integral of the airway acoustic echo 170. In the present embodiment, the user interface 350 illustrates the lung parameter 180 as a shaded area bounded by the echo signal 176 of the airway acoustic echo 170 and a time delay axis 352. Moreover, a numerical representation 354 of the current airway openness may be displayed in alternative or in addition to the sound pressure waveform 152. Further, should the method 300 of FIG. 4 have been recently performed (e.g., within a time threshold), the user interface 350 may include an indication 356 that a minimum effective pressure of the ventilator 22 has been reached.

As mentioned above, the monitor 24 includes the monitor housing 82 to which the display 84 and the user-selectable buttons 90 may be coupled. In some embodiments, the user-selectable buttons 90 and/or a touch sensor of the display 84 may permit the medical provider to provide input to the monitor 24. For example, the medical provider may actuate various care-facilitating features of the monitor 24, including a store baseline option 360, a log treatments option 362, an adjust pressure option 364, and/or an adjust gas mixture option 366. In some cases, when other treatment subsystems are communicatively coupled to the monitor 24, the monitor 24 may also be configured to receive user input that causes the monitor 24 to actuate the other treatment subsystems, such as the surfactant system 100, the suctioning system 102, and/or the patient positioning system 104.

Figure 7:
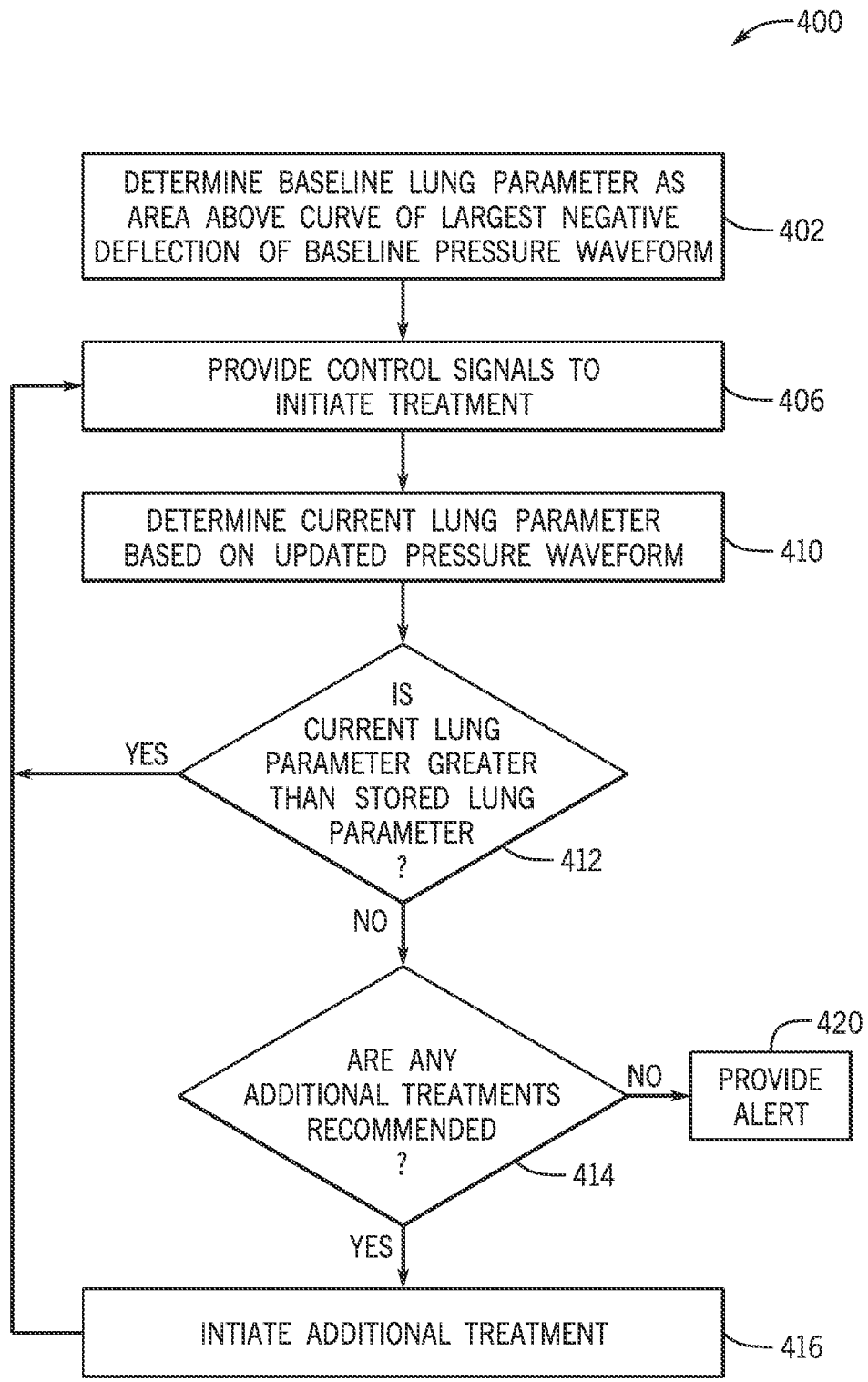
FIG. 7 is a flow diagram of a method of operating the airway management system of FIG. 1 to control atelectasis treatment, in accordance with certain embodiments of the present disclosure.

Moreover, the airway management system 20 may facilitate closed-loop performance of multiple treatments for the patient, such as based on a schedule or treatment plan input to the monitor 24 by a medical provider. For example, FIG. 7 is a flow diagram of a method 400 for coordinating multiple atelectasis treatments with the airway management system 20. The method is generally indicated by reference number 400 and includes various steps or actions represented by blocks, which may be performed by the processor 80 of the monitor 24, in an embodiment. The method 400 begins with the processor 80 determining, at step 402, the baseline lung parameter for the patient 40, which may be calculated as the area above the curve of the airway acoustic echo discussed above. At step 404, the processor 80 may select a current treatment for atelectasis, such as based on the baseline lung parameter. For example, in response to determining that the baseline lung parameter is indicative of a high extent of atelectasis, the current treatment may be selected as the treatment most likely to cause substantial airway recruitment. In an embodiment, the medical provider may provide a treatment schedule to the monitor 24, such as a treatment schedule recommending that the monitor 24 sequentially actuate a particular order of treatments, with each treatment to be actuated as long as recruitment is detected.

Thus, at step 406, the processor 80 may provide control signals to cause the current treatment. For example, the current treatment may be directed to adjusting the settings of the ventilator 22. During or after the treatment, the processor 80 may determine, at step 410, a current lung parameter based on updated sound pressure waveform received from the acoustic sensor 26, as discussed above. At step 412, the processor 80 may determine whether the current lung parameter is greater than the previous lung parameter, such as by a threshold amount or percentage difference. In response to determining that the treatment caused the lung parameter to suitably increase, such as by more than a threshold amount or percentage, the processor 80 may return to step 406 to provide additional control signals that cause additional application or continued performance of the current treatment.

In response to determining that the current lung parameter is not suitably increased relative to the previous lung parameter, the processor 80 may determine whether any additional treatments are recommended, at step 414. In an embodiment, the processor 80 may determine whether another treatment is listed or included on the treatment schedule. For example, after adjusting the pressure settings of the ventilator 22, the processor 80 may identify that adjusting the composition of the gas mixture 70, instilling surfactant, suctioning the airway, and/or repositioning the patient 40 is recommended on the treatment schedule. In response to determining that an additional treatment is recommended, the processor 80 may select, at step 416, an additional treatment as the current treatment, then return to step 406 to optimize or increase the lung parameter via performance of the additional treatment. The processor 80 may continue to coordinate operation of the airway management system 20 to systematically perform multiple atelectasis treatments based on monitored lung parameters of airway openness, in a closed loop manner. Then, in response to determining that each recommended treatment has been performed to suitably address atelectasis, the processor 80 may provide, at step 420, an alert indicative of the atelectasis treatment schedule being performed.

Figure 8:
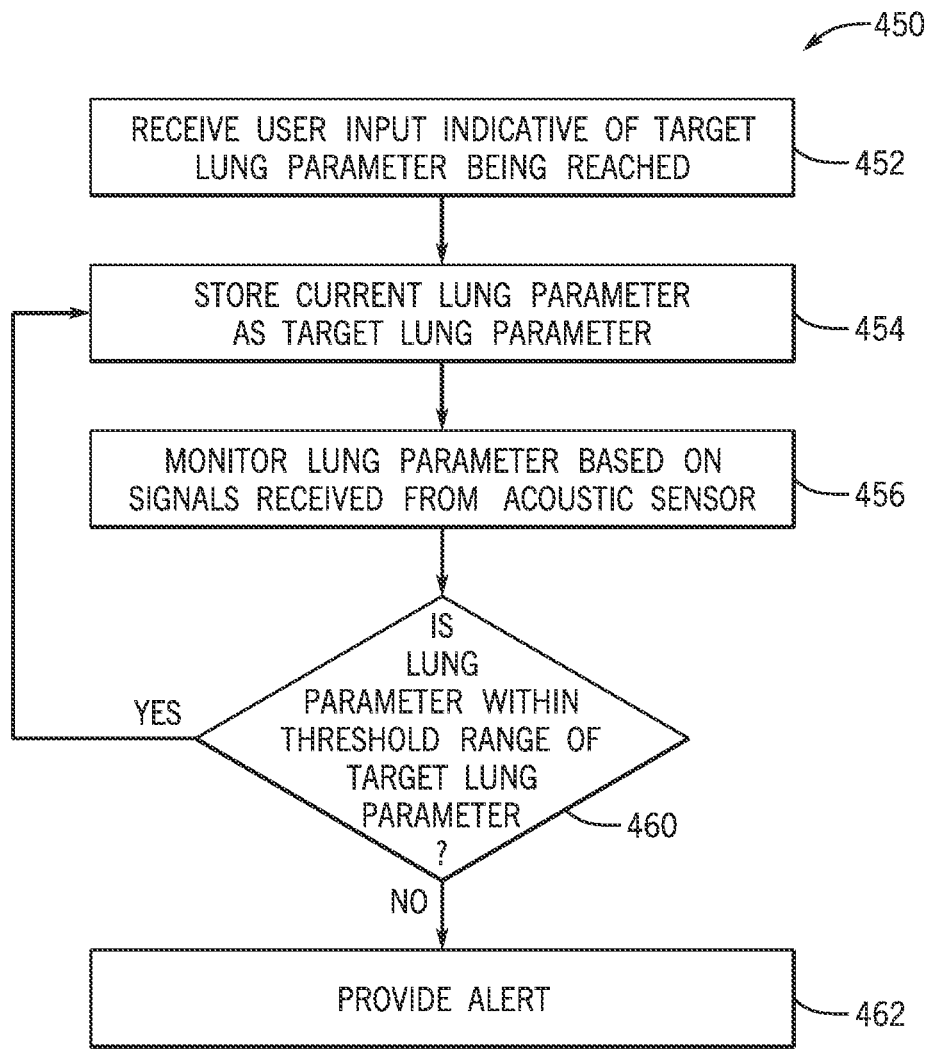
FIG. 8 is a flow diagram of a method of operating the airway management system of FIG. 1 to provide continuous airway openness monitoring, in accordance with certain embodiments of the present disclosure.

FIG. 8 is a flow diagram of a method 450 of operating the airway management system 20 to monitor airway openness of the patient 40 over a period of time, in accordance with some embodiments. The method is generally indicated by reference number 450 and includes various steps or actions represented by blocks, which may be performed by the processor 80 of the monitor 24, in an embodiment. In an embodiment, the method 450 may be performed after any of the methods 250, 300, 400 are performed to ensure a pulmonary condition of the patient 40 remains in a stable range for the duration of ventilation of the patient 40.

In the illustrated embodiment, the method 450 begins with the processor 80 receiving, at step 452, user input indicative of a target lung parameter of airway openness being reached. In some embodiments, the processor 80 receives the user input via the user-selectable buttons 90, via a touch sensor of the display 84, via selection of the store baseline option 360, or by another suitable input device. In some embodiments, the user input is provided after one or multiple atelectasis treatments that increase airway openness are performed, as discussed above. Then, at step 454, the processor 80 stores a current lung parameter of the patient 40 as a target lung parameter. That is, the sensor signal acquired from the acoustic sensor 26 at the time of receiving the user input is stored as a calibration or characteristic signal indicative of the target airway openness. The monitor 24 may therefore leverage the current lung parameter as a baseline lung parameter that facilitates appropriate long-term monitoring of the lungs 64.

At step 456, the processor 80 may monitor an updated lung parameter based on updated signals received from the acoustic sensor 26. Indeed, the acoustic sensor 26 may continuously provide sensor signals to the monitor 24, such that the monitor 24 may continuously analyze the airway acoustic echo for updated instances of the lung parameter. The monitor 24 may therefore determine, at step 460, whether the updated lung parameter is within a threshold range of the target lung parameter. It should be understood that the threshold range may be set to any suitable range corresponding to an acceptable amount of deviation of the lung parameter from the target lung parameter. For example, the threshold range may be set as a 1 percent deviation, a 3 percent deviation, a 5 percent deviation, a 10 percent deviation, and so forth. Further, the threshold range may be a patient-calibrated range, in which patients 40 having a lesser airway openness may be monitored with a correspondingly reduced threshold range.

In response to determining that the updated lung parameter is within the threshold range of the target lung parameter, the processor 80 determines that the airway openness of the patient 40 remains within a suitable range, and returns to step 456 to continue monitoring the lung parameter of airway openness. In some embodiments, the processor 80 may evaluate the lung parameter continuously or at a regular basis (e.g., every rest phase of breathing cycles). Alternatively, in response to determining that the current lung parameter is not within the threshold range of the target lung parameter, the processor 80 may, at step 462, provide an alert or instructions indicative of the variation in the lung parameter. The alert provided by the processor 80 of the monitor 24 may include any suitable audible or visible indication of the change in airway openness. For example, the processor 80 may instruct the display 84 of the monitor or a dedicated mobile application of a smart phone or mobile device to alert the medical provider of the change in airway openness. Via the method 450, the airway management system 20 may therefore efficiently provide closed loop control features that enhance the long-term ventilation of the patient 40.

Figure 9:
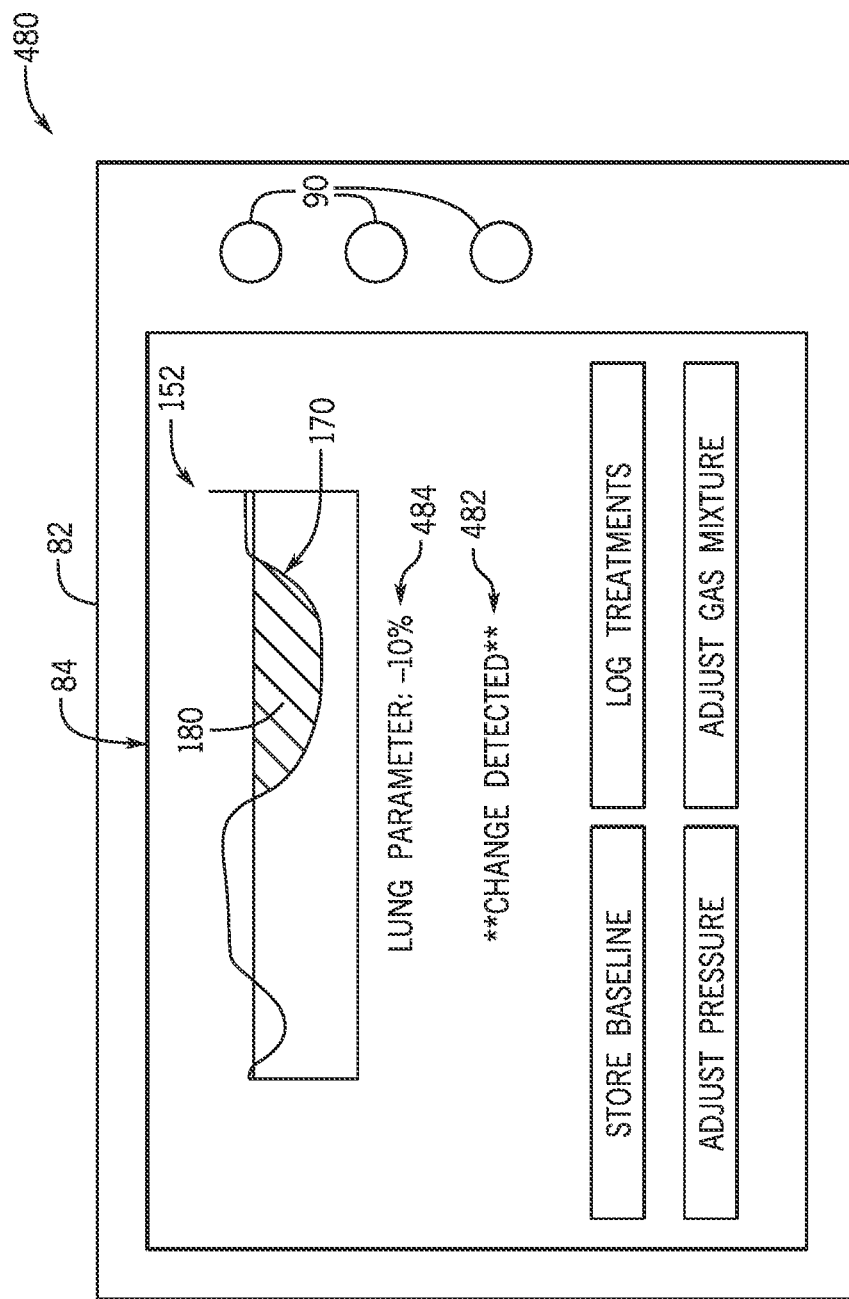
FIG. 9 is a schematic illustration of a user interface for the monitor of the airway management system, in accordance with certain embodiments of the present disclosure.

Indeed, as illustrated, FIG. 9 is a schematic illustration of a user interface 480 for the display 84 of the monitor 24. The user interface 480 may display an alert indication 482 that indicates a threshold deviation in the lung parameter 180 determined from the airway acoustic echo 170 relative to the baseline lung parameter. In some embodiments, the alert indication 482 may include or be accompanied by a quantification 484 of the deviation, permitting the medical provider to recommend subsequent atelectasis treatments to address the changing airway openness. In an embodiment, the monitor 24 may continuously display a percent change of the lung parameter 180 relative to the baseline lung parameter as the quantification 484 to provide continuous information to the medical provider that facilitates efficient patient care.

The airway management system provided herein may be used during the course of ventilation of a patient to facilitate or actively deliver treatments for various pulmonary disorders, such as atelectasis. For example, the patient may be ventilated through a tracheal tube that is equipped with an acoustic sensor having an acoustic generator and an acoustic receiver. By selectively directing sound energy through the tracheal tube and receiving reflections or echoes back from lungs of the patient, the acoustic sensor may provide sensor signals indicative of sound pressure waveforms to a monitor of the airway management system. The monitor may analyze (e.g., integrate) an airway acoustic echo of the sound pressure waveform to identify a lung parameter indicative of a total cross-sectional area, or volume, of airways within the lungs. As such, the monitor leverages acoustic reflectometry techniques to monitor lung parameters of airway openness for the patient. Continuous real-time monitoring of airway openness facilitates more accurate identification of patients in need of treatment to address insufficient airway openness and more accurate assessment of the treatments administered to these patients, thus more efficiently distributing resources in a healthcare setting. Equipped with this real-time monitoring of the state of the lungs, medical providers may perform informed treatments for atelectasis, where immediate results regarding whether a treatment is successful in recruiting airways may be presented on the monitor. In some cases, the monitor may also directly control treatment subsystems of the airway management system to provide suitable treatments or clinical interventions. Indeed, as one example, the monitor may control or be integrated with a ventilator to iteratively identify a minimum effective ventilator pressure for recruitment, in a closed-loop manner. In some cases, the monitor may also facilitate monitoring of airway openness over time, such as by presenting alerts or coordinating treatments in situations in which the lung parameter of the patient deviates by more than a predetermined amount.

While the disclosed embodiments have been discussed in the context of atelectasis, the airway management system provided herein may be used to identify, monitor, and/or treat patients with reductions in airway openness having other disorders, using the treatments disclosed herein. Examples of such disorders include pneumothorax or associated lung collapse. The disclosed techniques may be used to identify sound pressure characteristic of flow from lung going out to the chest wall/thorax instead of returning through ETT and out the ventilator circuit that is indicative of pneumothorax. In one example, the disclosed techniques may be used to identify asthma, wheezing, exacerbation or start of attacks for asthmatics, emphysematics, COPDers, reactive airways disease, and inflammation and/or spasms of the airways beyond the carina. Additional examples of such disorders include pneumonia or other infections that affect alveoli, pleural effusions (e.g., associated with pneumonia, cancer, CHF), space occupying lesions (tumors, cancer, sarcoidosis, idiopathic pulmonary fibrosis).

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A system, comprising:
a tracheal tube positioned within an airway of a ventilated patient;
an acoustic sensor coupled to the tracheal tube; and
a monitor communicatively coupled to the acoustic sensor, wherein the monitor comprises a processor, and wherein the processor is configured to:
receive a baseline signal from the acoustic sensor;
provide control instructions to adjust one or more ventilatory parameters to deliver a gas mixture to the airway through the tracheal tube;
receive an updated signal from the acoustic sensor after the adjustment; and
identify a change in airway openness of lungs of the ventilated patient caused by the adjustment of the one or more ventilatory parameters, wherein identifying the change is based on the baseline signal and the updated signal.

2. The system of claim 1, wherein the baseline signal is indicative of a baseline sound pressure waveform having a negative deflection, and wherein an area above a curve of the negative deflection is indicative of a baseline airway openness of the lungs of the ventilated patient.

3. The system of claim 1, wherein the change in the airway openness comprises an increase in the airway openness, and wherein the processor is configured to provide additional control instructions to further adjust the one or more ventilatory parameters in response to identifying the change.

4. The system of claim 3, wherein the processor is configured to:
identify no additional increase in the airway openness caused by the further adjustment of the one or more ventilatory parameters;
identify a setting of the one or more ventilatory parameters at a time point before the further adjustment; and
provide additional control instructions to return to the setting.

5. The system of claim 4, wherein the processor is configured to provide further control instructions to maintain the setting in response to a threshold time period elapsing.

6. The system of claim 1, comprising a ventilator coupled to a source of the gas mixture and communicatively coupled to the monitor, wherein the processor is configured to provide the control instructions to the ventilator to adjust one or more ventilatory parameters.

7. The system of claim 1, wherein a first end of the acoustic sensor is coupled to the tracheal tube, wherein the system comprises a ventilator coupled to a second end of the acoustic sensor, and wherein the processor is configured to provide additional control instructions to the ventilator to change a composition of the gas mixture to comprise a bronchodilator or other inhaled medications, in response to identifying the change.

8. The system of claim 1, comprising a surfactant system communicatively coupled to the monitor, wherein the processor is configured to provide additional control instructions to the surfactant system to initiate application of a surfactant through the tracheal tube in response to identifying the change.

9. The system of claim 1, wherein the monitor comprises a display, and wherein, in response to identifying the change, the processor is configured to provide control signals to cause the display to present an indication recommending repositioning of the ventilated patient, suctioning of the airway, instilling surfactant into the lungs, or a combination thereof.

10. The system of claim 1, wherein the acoustic sensor comprises an acoustic generator oriented to emit sound energy into the tracheal tube and an acoustic receiver configured to detect reflected sound energy from the airway.

11. The system of claim 1, wherein the one or more ventilatory parameters comprise gas mixture composition, pressure, tidal volume, minute volume, peak pressure, respiratory frequency, positive end expiratory pressure, inspiratory time, inspiratory flow, inspiratory-to-expiratory ratio, time of pause, trigger sensitivity, support pressure, expiratory trigger sensitivity, or a combination thereof.

12. A method, comprising:
receiving, at a ventilator monitor, sensor signals indicative of a sound pressure waveform from an acoustic sensor that is coupled to a tracheal tube positioned within an airway of a ventilated patient;
identifying changes in the sound pressure waveform concurrent with a treatment of atelectasis; and
providing an indication that the changes are indicative of increasing airway openness, decreasing airway openness, or unchanging airway openness.

13. The method of claim 12, wherein identifying changes in the sound pressure waveform comprises analyzing that an area above a curve of a negative deflection of the sound pressure waveform is changed.

14. The method of claim 12, comprising controlling a ventilator to provide the treatment by adjusting one or more ventilatory parameters.

15. The method of claim 14, wherein the one or more ventilatory parameters comprise gas mixture composition, pressure, tidal volume, minute volume, peak pressure, respiratory frequency, positive end expiratory pressure, inspiratory time, inspiratory flow, inspiratory-to-expiratory ratio, time of pause, trigger sensitivity, support pressure, expiratory trigger sensitivity, or a combination thereof.

16. The method of claim 12, comprising controlling a positioning actuator of a patient positioning system to perform the treatment by changing a position of the ventilated patient.

17. The method of claim 12, comprising:
receiving, at the ventilator monitor, a user input that a current airway openness is a target airway openness;
identifying additional changes in the sound pressure waveform after the treatment;
determining that the additional changes are indicative of subsequent decreasing airway openness relative to the target airway openness; and
providing an additional indication of the subsequent decreasing airway openness.

18. A monitor configured to control ventilation of a patient, comprising:
a communication component configured to communicate sensor signals from an acoustic sensor that is coupled to a tracheal tube positioned within a patient airway;
a display; and
a processor communicatively coupled to the communication component and the display, wherein the processor is configured to:
receive the sensor signals indicative of a sound pressure waveform from the acoustic sensor;

analyze a negative deflection of the sound pressure waveform to determine a state of airway openness of lungs of the patient; and instruct the display to provide an indication of the state of airway openness.

19. The monitor of claim 18, wherein the processor is configured to:

receive updated sensor signals during or after a treatment of atelectasis; and instruct the display to provide an updated indication of the state of airway openness during or after the treatment, wherein the state of airway openness is based on an area above a curve of an updated negative deflection associated with the updated sensor signals.

20. The monitor of claim 19, wherein the treatment comprises adjusting a ventilatory parameter.

21. The monitor of claim 18, wherein the monitor is communicatively coupled to a ventilator configured to provide a gas mixture through the tracheal tube, and wherein the processor is configured to provide control signals to instruct the ventilator to iteratively increase a pressure of the gas mixture by a threshold pressure increment until the state of airway openness does not change beyond a predetermined amount.

22. The monitor of claim 21, wherein the processor is configured to instruct the ventilator to decrease the pressure of the gas mixture to a maintenance pressure in response to a threshold time period elapsing after the state of airway openness does not change beyond the predetermined amount.

23. A system, comprising:

a tracheal tube positioned within an airway of a ventilated patient;

an acoustic sensor coupled to the tracheal tube; and a monitor communicatively coupled to the acoustic sensor, wherein the monitor comprises a processor, and wherein the processor is configured to:

receive a signal from the acoustic sensor;

provide control instructions to initiate titration of one or more ventilatory parameters to deliver a gas mixture to the airway through the tracheal tube based on the signal;

receive updated signals from the acoustic sensor during the titration; and identify a setting of the one or more ventilatory parameters associated with sufficient adjustment based on the updated signals from the acoustic sensor.

24. The system of claim 23, wherein the one or more ventilatory parameters comprise ventilatory parameters of positive end-expiratory pressure ventilation.

25. The system of claim 23, wherein the control instructions to titrate one or more ventilatory parameters comprise instructions to adjust the one or more ventilatory parameters in a stepwise manner.

* * * * *